United States Patent [19]
Delannoy et al.

[11] Patent Number: 5,284,144
[45] Date of Patent: Feb. 8, 1994

[54] APPARATUS FOR HYPERTHERMIA TREATMENT OF CANCER

[75] Inventors: Jose Delannoy, Monsen Baroeul, France; Denis Le Bihan, Rockville, Md.; Ching-nien Chen, Catonsville, Md.; Ronald L. Levin, Olney, Md.; Robert Turner, Bethesda, Md.

[73] Assignee: The United States of America as represented by the Secretary of the Dept. of Health & Human Services, Washington, D.C.

[21] Appl. No.: 35,536

[22] Filed: Mar. 22, 1993

Related U.S. Application Data

[63] Continuation of Ser. No. 735,682, Jul. 29, 1991, abandoned, which is a continuation of Ser. No. 439,661, Nov. 22, 1989, abandoned.

[51] Int. Cl.$^5$ ............................................. A61B 5/055
[52] U.S. Cl. ........................... 128/653.2; 128/24 AA; 128/736; 324/315; 607/154
[58] Field of Search ................ 128/653.2, 653.5, 804, 128/399, 736, 24 AA; 324/315, 309, 318, 322

[56] References Cited

U.S. PATENT DOCUMENTS

| | | |
|---|---|---|
| 3,839,641 | 6/1973 | Cooke et al. . |
| 3,991,770 | 12/1975 | LeVeen . |
| 4,186,729 | 11/1977 | Harrison . |
| 4,230,129 | 4/1976 | LeVeen . |
| 4,254,778 | 3/1981 | Clow et al. ...................... 128/653 A |
| 4,346,716 | 3/1980 | Carr . |
| 4,479,498 | 8/1982 | Toftness . |
| 4,554,925 | 11/1985 | Young .............................. 128/653 A |
| 4,589,423 | 5/1986 | Turner ................................... 128/804 |
| 4,632,128 | 6/1985 | Paglione et al. . |
| 4,665,364 | 5/1987 | Hanawa ............................ 127/653 |
| 4,719,425 | 1/1988 | Ettinger .......................... 128/653 A |
| 4,798,209 | 1/1989 | Klingenbeck et al. ......... 128/653 R |
| 4,809,701 | 3/1989 | Le Bihan et al. ............... 128/653 A |
| 4,815,479 | 8/1986 | Carr . |
| 4,820,983 | 4/1989 | Bendall et al. ....................... 324/309 |
| 4,848,362 | 12/1986 | Larsen . |
| 4,914,608 | 4/1990 | Le Bihan et al. ................... 324/315 |
| 4,951,668 | 8/1990 | Keren .............................. 128/653 A |
| 4,977,902 | 12/1990 | Sekino et al. ........................ 128/804 |

OTHER PUBLICATIONS

Crooks, "NMR Hardware in Imaging" in *Nuclear Magnetic Resonance Imaging in Medicine*, Edited by Kaufman et al. Igaku-Shoin Ltd, (1982) p. 56.

British Application No. 14434 corresponding with published British Application No. 2,183,322 published Feb. 3, 1988.

Guerquin-Kern et al., "Experimental Characterization of the Mini-Annular Phased Array as a Hypothermia Applicator," submitted to *Medical Physics*, Jun. 1986 and May 1987 (revised).

*Primary Examiner*—Ruth S. Smith
*Attorney, Agent, or Firm*—Lowe, Price, LeBlanc & Becker

[57] ABSTRACT

A hyperthermia applicator/MRI probe assembly for hyperthermia treatment of a subject. The assembly includes a hyperthermia applicator for heating target regions of a subject and a MRI probe which is utilized to monitor temperatures within the heating region. The hyperthermia applicator and MRI probe are coupled to a control system which receives information from the MRI probe and utilizes the information to control the hyperthermia applicator so as to maintain constant, desired temperatures within the heating region. The hyperthermia applicator/MRI probe assembly of the present invention allows for temperature control within about 0.5° C.

19 Claims, 7 Drawing Sheets

APPARATUS FOR HYPERTHERMIA TREATMENT OF CANCER

This application is a continuation application of application Ser. No. 07/735,682, filed Jul. 29, 1991, now abandoned, which is a continuation application of application Ser. No. 07/439,661 filed Nov. 22, 1989, now abandoned.

FIELD OF THE INVENTION

This invention relates to an apparatus for hyperthermia treatment which comprises a combination hyperthermia unit/MRI probe. Moreover, this invention also relates to an MRI apparatus which utilizes the combination hyperthermia unit/MRI probe disclosed herein. The apparatus is useful for the treatment of e.g., cancer usually as an adjunct to chemotherapy, and/or radiotherapy.

BACKGROUND OF THE INVENTION

Many clinical studies have shown the effectiveness of hyperthermia (HT) as an adjunctive treatment for malignancies, when used in combination with radiotherapy or chemotherapy (Hahn G. M., Hyperthermia and Cancer, 2nd Ed., New York, Plenum, (1982); Scott, R. S. et al, Int. J. Rad. Oc. Biol. Phys. (10(11) 2219-2123, (1984); Lindholm, C. E. et al, Rec. Res. in Cancer Res. 107: 152-156 (1988)).

Efficacy requires that temperatures within a tumor(s) remain above about 43° C. for 30 to 60 minutes, while safety considerations limit temperatures in normal tissues to below 42° C. In hyperthermia treatment, it is therefore necessary to control the temperature throughout the heated volume to better than about 1° C.

Over the past several years, hyperthermia devices have been improved significantly so that it is now possible to focus energy into a given region of the body (Hahn G. M., Hyperthermia and Cancer, 2nd Ed., New York, Plenum, (1982); Field, S. F. and Franconi, C., Technology of Hyperthermia, Dordrecht, Martinus Nijhoff Publishers (1987)). Despite these advances, however, a lack of adequate temperature control has heretofore limited the usefulness of such devices.

Temperatures can be measured with good accuracy by invasive means. This is attained by means such as thermocouples, thermistors or fiber-optic probes. However, only regions in close proximity to the probes can be monitored with these technologies (Gibbs, F. A. et al, Hyperthermic Oncology, 1st Edition, Vol 2, Philadelphia: Taylor and Francis, pp. 155-167 (1984); Cetas, T. C. Cancer Res. (suppl) 44: 4805-4808 (1984)). Furthermore, probe insertion may be painful and hazardous. Various non-invasive methods have previously been proposed to monitor temperature during hyperthermia. It is, however, difficult to achieve deep measurements with microwave radiometry or infrared thermography while ultra-sound, computerized tomography (CT) and active microwave techniques lack the required accuracy or resolution necessary for controlled treatment.

Magnetic resonance imaging (MRI) is a non-invasive and non-ionizing technique which produces anatomical images in any orientation. Its use as a means to "map" temperature was suggested several years ago (Parker, D. L. et al, Med. Phys 10(3): 321-325 (1983); Dickinson, R. J. et al, J. Comput Assist Tomogr. 10(3): 468-472 (1986); Tanaka, H. et al, Nippon Acta Radiol. 41:897-899 (1981)). Unfortunately, these attempts were unsuccessful because the parameter used, the relaxation time $T_1$, is difficult to measure accurately by MRI and may have a complex relation with temperature (Lewa, C. J. and Majewska, Z., Bull. Cancer (Paris), 67: 525-530 (1980); Jolesz, F. Z. et al, Radiology 168: 49-253 (1988)).

On the other hand, there is a well known relationship between molecular diffusion and temperature (Simpson, J. H. and Carr, H. Y., Phys. Rev. 111: 1201-1202 (1958)).

It was recently shown that temperature imaging in phantoms can be obtained with good accuracy and resolution (better than 0.5° C./cm) by means of magnetic resonance imaging of molecular diffusion (LeBihan, D. et al, Radiology 171: 853-587 (1989); U.S. patent application Ser. No. 07/324,101 filed on Aug. 19, 1988 by the present inventors, the text of which describes the method of imaging molecular diffusion by NMR is incorporated herein by reference). The same technique was also shown useful to evaluate tissue perfusion (LeBihan, D. et al, Radiology 168: 497-505 (1988)), the dominant physiological mechanism for removing heat during hyperthermia (Hahn, G. M., Physica and Technology of Hyperthermia, Boston: Martinus Nijhoff Publisher, pp. 441-447 (1987); Shitzer, A. and Eberhart, R. C. Ed. Heat Transfer in Medicine and Biology, New York: Plenum (1985); Delannoy, J. et al, Int. J. Hyperthermia (1989), in press). Also, recently it was speculated that MR spectroscopy can be useful to monitor tumor metabolism (Vaupel, P. W. et al, Proc. SMRM, Vol. 1, p. 412 (1988)).

U.S. Pat. No. 4,230,129 to Le Veen discloses a method of heating body tissue and monitoring temperature changes in the tumor in real time with the aid of a scintillation detector. The method provides for the coupling of RF energy to the patient's body to avoid any significant heat absorption in the fatty tissues. This is obtained by focusing the RF energy on the tumor with an orbital movement of the applicator so that energy is not constantly being applied to the same confined area within the patient's body. U.S. Pat. No. 3,991,770 to Le Veen issued from the parent application U.S. Pat. No. 4,230,129 to Le Veen and has claims directed to a method of treating a tumor in a human by placing the part of the human body containing the tumor in a radiofrequency electromagnetic field to heat the tumor tissue and cause necrosis of the tumor without damaging the adjacent normal tissue.

U.S. Pat. No. 4,186,729 to Harrison discloses an improved electrode for use with an apparatus employing RF energy to produce RF-induced hyperthermia of living animal tissue. The temperature is measured by means of an inserted thermistor.

U.S. Pat. No. 4,346,716 to Carr discloses a microwave system applied to the detection of cancerous tumors. The system combines in a single unit a passive radiometer with an active microwave transmitter in a hand-held unit for heating subsurface tissue. It also provides a radiometer for the remote detection of temperature.

U.S. Pat. No. 4,848,362 to Larsen provides a method for therapeutic deep heating of musculoskeletal tissue with an improved transducer serving simultaneously to couple power from a generator into the patient and to sense the therapeutic response produced. A single unit generates a heating RF signal and detects its thermal response. The response is then used to control the treatment. Both heating and sensing are accomplished by one transducer and one apparatus if dielectric heating is employed. If other forms of heating are used, e.g., ultrasound, the sensor still is present but the apparatus is modified by replacing the high power electromagnetic source with a low power source version.

U.S. Pat. No. 4,815,479 to Carr provides a system and associated method combining microwave detection (radiometry) with microwave heating (hyperthermia) for the treatment of cancer. A plurality of antennas are provided which are disposed over the tumor site in order to separate signal channels. This permits the adjustment of the phase of the separate antenna signals to maximize the signal detected at the microwave radiometric detector.

U.S. Pat. No. 4,632,128 to Paglioni et al. discloses an apparatus for heating which includes an antenna provided with at least one convolution of conductor centered on an axis, the antenna being adapted for heating a surface upon receipt of electrical power. A non-contacting temperature sensor is provided centered on the axis of the antenna with a field of view directed along that axis. A method of analysis and corrective adjustment for relief of nerve interference in the human body is provided which scans subcutaneous microwave emissions of the spinal column, collects and converts the emissions into a visual output, compares with a normal pattern of emissions, determines areas of deviation pinpointing stress, applies a manual corrective adjustment to the spinal column, and monitors throughout the corrective treatment.

None of the methods known in the art and described above provide the simultaneous capability of a hyperthermia applicator and the MRI monitoring of the temperature produced in a human body part during treatment.

Accordingly, there is still a need for an improved apparatus for hyperthermia treatment.

SUMMARY OF THE INVENTION

This invention relates to an apparatus for hyperthermia treatment of a subject comprising a combined hyperthermia applicator/MRI probe comprising an MRI probe that includes a tuning/matching circuit and a radiofrequency coil for receiving and transmitting magnetic resonance signals, said tuning/matching circuit and radiofrequency coil being operably connected to one another and said coil being positioned inside a magnet to provide information which permits the control of the amount of radiant energy transmitted by a hyperthermia applicator to control and/or maintain the temperature at the subject's body part being treated within about ±0.5° C.;

a hyperthermia applicator which when activated by a signal can transmit radiant energy, said applicator being positioned inside the MRI probe and being provided with an inner surface for exposure to a subject's target body part to be treated;

a filter operably connected either to the applicator or the probe to isolate the signals thereof from one another; and a conformable filler covering the surface of the hyperthermic applicator said filler being capable of transmitting radiant energy from the applicator to the subject's body part to be treated; wherein all components of the apparatus are made of substantially non-ferromagnetic materials.

This invention also encompasses an apparatus, comprising a magnetic gradient coil for recording diffusion images and/or for fast acquisition of images, said gradient coil means being positioned outside a hyperthermia applicator;

an MRI probe that includes a tuning/matching circuit and a radiofrequency coil for receiving and transmitting magnetic resonance signals, said tuning/matching circuit and radiofrequency coil being operably connected to one another and said coil being positioned inside a magnet to provide information which permits the control of the amount of radiant energy transmitted by a hyperthermia applicator to control and/or maintain the temperature at the subject's body part being treated within about ±0.5° C.;

a hyperthermia applicator which when activated by a signal can transmit radiant energy, said applicator being positioned inside the MRI probe and being provided with an inner surface for exposure to a subject's target body part to be treated;

a filter operably connected either to the applicator or the probe to isolate the signals thereof from one another; and a conformable filler covering the surface of the hyperthermic applicator said filler being capable of transmitting radiant energy from the applicator to the subject's body part to be treated; wherein all components of the apparatus are made of substantially non-ferromagnetic materials.

Also part of this invention is an MRI apparatus, comprising a magnetic field gradient coil means for recording diffusion images and/or for fast acquisition of images positioned outside a hyperthermia applicator means;

a magnet producing a magnetic field of about 0.01 to 10 tesla; and an apparatus for hyperthermia treatment comprising a combination hyperthermia applicator/MRI probe, which comprises an MRI probe that includes a tuning/matching circuit and a radiofrequency coil for receiving and transmitting magnetic resonance signals, said tuning/matching circuit and radiofrequency coil being operably connected to one another and said radiofrequency coil being positioned inside a magnet to provide information which permits the control of the amount of radiant energy transmitted by a hyperthermia applicator to control and/or maintain the temperature at the subject's body part being treated within about ±0.5° C.; a hyperthermia applicator which when activated by a signal can transmit radiant energy, said applicator being positioned inside the MRI probe and being provided with an inner surface for exposure to a subject's target body part to be treated; a filter operably connected either to the applicator or the probe to isolate the signals thereof from one another; and a conformable filler covering the surface of the hyperthermic applicator, said filler being capable of transmitting radiant energy from the applicator to the subject's body part to be treated; wherein all components of the apparatus are made of substantially non-ferromagnetic materials.

A more complete appreciation of the invention and many of the attendant advantages thereof will be readily perceived as the same becomes better understood by references to the following detailed description when considered in connection with the accompanying figures.

Figure 1:
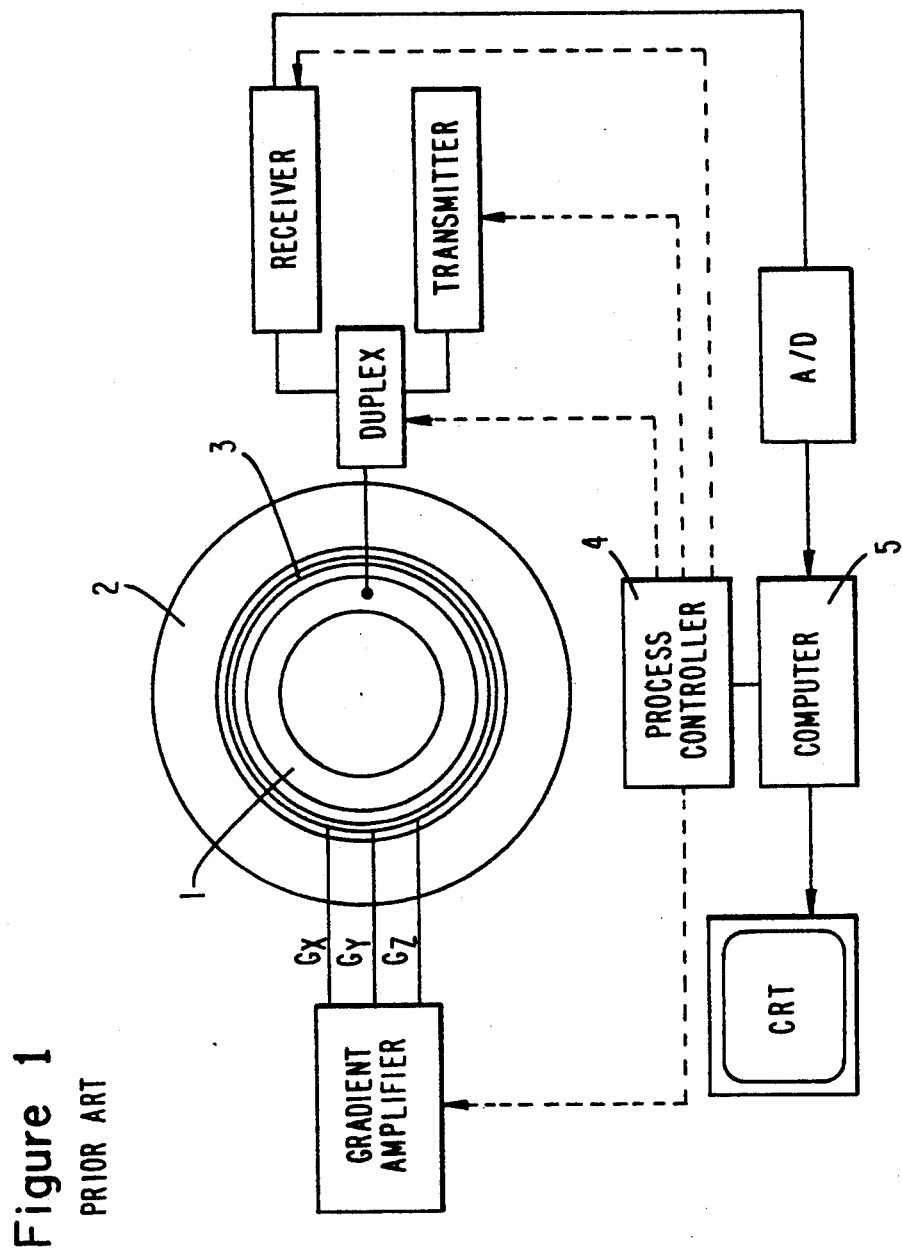
FIG. 1 shows a diagram of a typical MRI unit.

Other objects, advantages and features of the present invention will become apparent to those skilled in the art from the following discussion.

DETAILED DESCRIPTION

This invention arose from a desire by the inventors to improve on prior art technology suitable for temperature-controlled hyperthermia treatment of patients.

Major drawbacks of using magnetic resonance techniques for the non-invasive monitoring of temperature and other physiological processes during clinical hyperthermia are the following.

(1) Despite the continuing increase in the number of MRI units, MRI procedures are expensive and HT treatments require 1 to 2 hour long periods, and (2) Current methods for temperature imaging only measure changes in temperature as opposed to the actual temperature.

(Simpson, J. H. and Carr, H. Y., Phys. Rev. 111: 1201-1202 (1958); LeBihan, D. et al, Radiology 171: 853-587 (1989)).

The first drawback poses a medical economics issue. Its resolution depends upon the efficacy of using MRI for monitoring temperature and other physiological processes non-invasively throughout the treatment area as opposed to using probes for monitoring temperature and/or perfusion invasively at a few pre-selected sites within the treatment area.

An advantage of the proposed apparatus is that it is easily removable from the MRI unit which can still be used for other purposes such as clinical imaging.

The second drawback can be circumvented by either one or two methods.

(1) The volume to be treated can be assumed to be at a relatively known homogeneous temperature. This is a reasonable assumption for abdominal or pelvic situations. Alternatively, the volume to be treated may be brought to a relatively known homogeneous temperature by surrounding it with a fluid-filled bolus maintained at normal body temperature. This is a reasonable assumption for limbs.

(2) Invasive probes at a few preselected sites in different types of tissues can be used to validate the MRI readings during the actual HT session.

The core of the magnetic resonance imaging system is a magnet, and most often a super-conducting magnet, which produces a strong homogeneous (several ppm) magnetic field, typically about 0.1 to 2 tesla for current clinical units. The resonant excitation of the atomic nuclei is achieved by the use of an additional transient rotating magnetic field, whose angular frequency depends directly on the main magnetic field strength and the type of nucleus. For the hydrogen nucleus generally used for medical imaging, this frequency is 42.6 MHz/tesla. Thus current MRI devices range in frequency from about 4.2 to 85 MHz. The rotating magnetic field is generated by radiofrequency pulses of about 1 to 20 kW transmitted by a coil surrounding the sample to be studied.

The resulting change in nuclear magnetization creates a component perpendicular to the main field rotating at the resonant frequency. This rotating nuclear magnet then induces a small signal, typically a few $\mu V$, in a receiving coil, which can be analyzed for imaging or spectroscopy purposes. However, the signal can be so small that the unit must be shielded from external radiofrequency sources.

To localize the measuring region, a set of "gradient" coils located between the MRI radiofrequency coils and the magnet may be used to generate spatial variations in the main magnetic field (see FIG. 1). These magnetic field gradients are switched rapidly during image acquisition and may generate eddy currents in any conductive part of the system. Such eddy currents are sources of image distortion and are best avoided by using actively shielded magnetic field gradient coils.

Heating is produced, in most cases, by depositing ultrasonic or electromagnetic energy directly into the tissues of interest. For the latter case, energy deposition in a given location depends on the local electric field strength and on the tissues' local dielectric characteristics.

Using a single, plane-wave, external, electromagnetic applicator, energy deposition usually is maximal at the skin surface and decreases more or less exponentially within depth. To reverse this trend, various types of multiple applicator systems have been proposed (Hahn G. M., Hyperthermia and Cancer, 2nd Ed., New York, Plenum, (1982); Field, S. F. and Franconi, C., Technology of Hyperthermia, Dordrecht, Martinus Nijhoff Publishers (1987); (Turner, P. F. IEEE Trans, MTT 34: 508-513 (1986); (Guerquin-Kern, J-L, et al, Medical Physics 14: 674-680 (1987); (Charny, C. et al, Medical Physics 13: 449-456 (1986); (Charny, C. et al, Medical Physics 15: 17-23 (1988)). These devices rely upon the phase and amplitude interaction of the fields emanating from each of their applicators to minimize energy deposition in the superficial layers and to maximize energy deposition in the deep regions. However, the resulting temperature distribution depends not only upon the energy deposition pattern but also upon the thermal clearance, mainly via perfusion, within the heated tissues (Hahn, G. M., Physics and Technology of Hyperthermia, Boston: Martinus Nijhoff Publisher, pp. 441-447 (1987); Shitzer, A. and Eberhart, R. C. Ed. Heat Transfer in Medicine and Biology, New York: Plenum (1985); Shitzer, A. and Eberhart, R. C. Ed. Heat Transfer in Medicine and Biology, New York:

Plenum (1985); Delannoy, J. et al, Int. J. Hyperthermia (1989). In press).

These factors make it difficult to predict the temperature distribution that will be achieved within the region to be treated.

Given the above descriptions of typical MR and HT systems, compatibility problems arise, inter alia, from the interactions of the strong magnetic field and the radiofrequency fields of the MRI system with the applicator of the HT system. The hyperthermia applicator of the invention must be made to work under such conditions and must be also physically compatible and fit inside the MR transmitting and receiving coil of the MRI probe.

An even more critical challenge, however, is to assure the correct operation of the MRI probe in the presence of the HT applicator. Any distortion of the main magnetic field of the MRI unit caused by the presence of any ferromagnetic parts must be eliminated. In addition, any perturbation of the radiofrequency field seen by the nuclei caused by the presence of the HT device must be eliminated as well.

Finally and perhaps most important, the MRI signal derived from the nuclei, which is of the order of nanowatts, must be purged of any radiofrequency pollution emanating from the hyperthermia applicators which are operating in a close frequency range at the level of several hundred watts.

The present technology unexpectedly attains these results and provides a hyperthermia apparatus capable of delivering heat treatment to a body part with a noninvasive temperature control of down to about 0.5° C., and preferably down to about 0.3° C. or less.

Thus, in accordance with the present invention it is provided herein an apparatus for hyperthermia treatment of a subject, which comprises a combination hyperthermia applicator/MRI probe means comprising an MRI probe that includes a tuning/matching circuit and a radiofrequency coil for receiving and transmitting magnetic resonance signals, the tuning/matching circuit and radiofrequency coil being operably connected to one another and said coil being positioned inside a magnet to provide information which permits the control of the amount of radiant energy transmitted by a hyperthermia applicator to control and/or maintain the temperature at the subject's body part being treated within about ±0.5° C.;

a applicator which when activated by a signal can transmit radiant energy, said applicator being positioned inside the coil and being provided with an inner surface for exposure to a subject's target body part to be treated;

a filter operably connected either to the applicator or the probe to isolate the signals thereof from one another; and a conformable filler covering the surface of the hyperthermic applicator, said filler being capable of transmitting radiant energy from the applicator to the subject's body part to be treated; wherein all components of the apparatus are made of substantially non-ferromagnetic materials.

The materials utilized for the manufacture of the applicator/probe of the invention must all be non-ferromagnetic. Examples of suitable materials are copper, aluminium and plastic. However, other materials may also be utilized.

The tuning/matching circuit and radiofrequency coil for receiving and transmitting magnetic resonant signals are known in the art and need not be described herein in further detail. (Alderman, D. N., and Grant D. M., J. Magn. Reson. 36, 447 (1979); Hoult, D. I., Chen C. N., Sank V. J., Magn. Reson. Med. 3, 730 (1986)).

The applicator/probe may further comprise other means which are known in the art of MRI probes.

The applicator/MRI probe is shaped in a manner such that it can easily be fitted inside a magnet of an MRI apparatus which is standard in the art.

The hyperthermia (HT) applicator is activated by a signal and transmits radiant energy. In different embodiments of the invention the HT applicator is activated and transmits radiofrequency waves, microwave radiation or ultrasound waves. In one particularly preferred embodiment the HT applicator comprises radiofrequency capacitive applicators of about 2 to 50 MHz, and more preferably about 5 to 35 MHz. In another preferred embodiment the HT applicator comprises a radiation applicator utilizing a radiofrequency of about 100 to 300 MHz, and more preferably about 150 to 250 MHz. In still another preferred embodiment the HT applicator utilizes microwave signals and comprises wave guides or microstrip applicators utilizing microwave radiation of about 300 MHz to 5 GHz, and more preferably about 500 MHz to 1 GHz. In still another preferred embodiment the HT applicator comprises piezoelectric applicators utilizing ultrasound radiation of about 0.1 to 20 MHz, and more preferably about 0.2 to 10 MHz.

In a most preferred embodiment the applicator/MRI probe of the invention, further comprises a magnetic gradient coil for recording diffusion images and/or for fast acquisition of images, said gradient coil positioned outside the hyperthermia applicator means.

Still more preferred is an applicator/MRI probe where the magnetic gradient coil has a gradient strength of about 20 to 100 mT/m and a rise time of less than about 100 μsec.

The magnetic gradient coil is selected from the group consisting of X-axis, Y-axis and Z-axis gradient coils and combinations thereof.

The magnetic gradient coil is preferably an Z-axis gradient coil.

In still another preferred embodiment the HT applicator comprises a mini annular phased array (MAPA) including antenna means for receiving incoming power and transmitting radiant energy to the subject's body part to be treated, e.g., a limb. Still more preferred is an apparatus where the HT applicator has an antenna means which comprises four pairs of dipole antenna, the members of each pair of antenna being symmetrically positioned with respect to the exposed surface of the applicator. For all practical purposes, a lower number of antenna pairs, although functional, yields lesser results. In a similar manner a number of pairs of antennas greater than 4 also increases complexity and is therefore less desirable although still suitable for use with the present invention.

Although the dipole antenna may be activated by signals of different frequencies having different amplitudes and phases, a preferred embodiment provides for the dipole antenna to be activated at a single frequency with signals of equal amplitude and phase.

In still another preferred embodiment the antenna means comprises antennas made of copper film of about 5 to 100 μm thick, and more preferably about 10 to 80

μm thick, to minimize eddy currents during gradient switching.

In still another preferred embodiment of the apparatus of the invention the MRI probe produces a rotating magnetic field with a resonant excitation signal of a frequency of about 2 to 100 MHz, and more preferably about 10 to 80 MHz and transmits to the subject's body part radiofrequency pulses of about 0.1 to 100 kW, and more preferably about 1 to 80 kW and the radio frequency coil receives a rotating field signal induced by the body part.

In still another preferred embodiment the apparatus of the invention further comprises cooling means positioned within the combination applicator/probe, said cooling means being capable of maintaining the temperature of the applicator/probe within a predetermined range;

a pump operably connected to the cooling means;

a heat-exchanger operably connected to the cooling means; and temperature measuring means operably connected to and for activating the heat-exchanger and the cooling means to maintain the temperature within the applicator/probe in an area of the subject's body surrounding the target part thereof.

Figure 4:
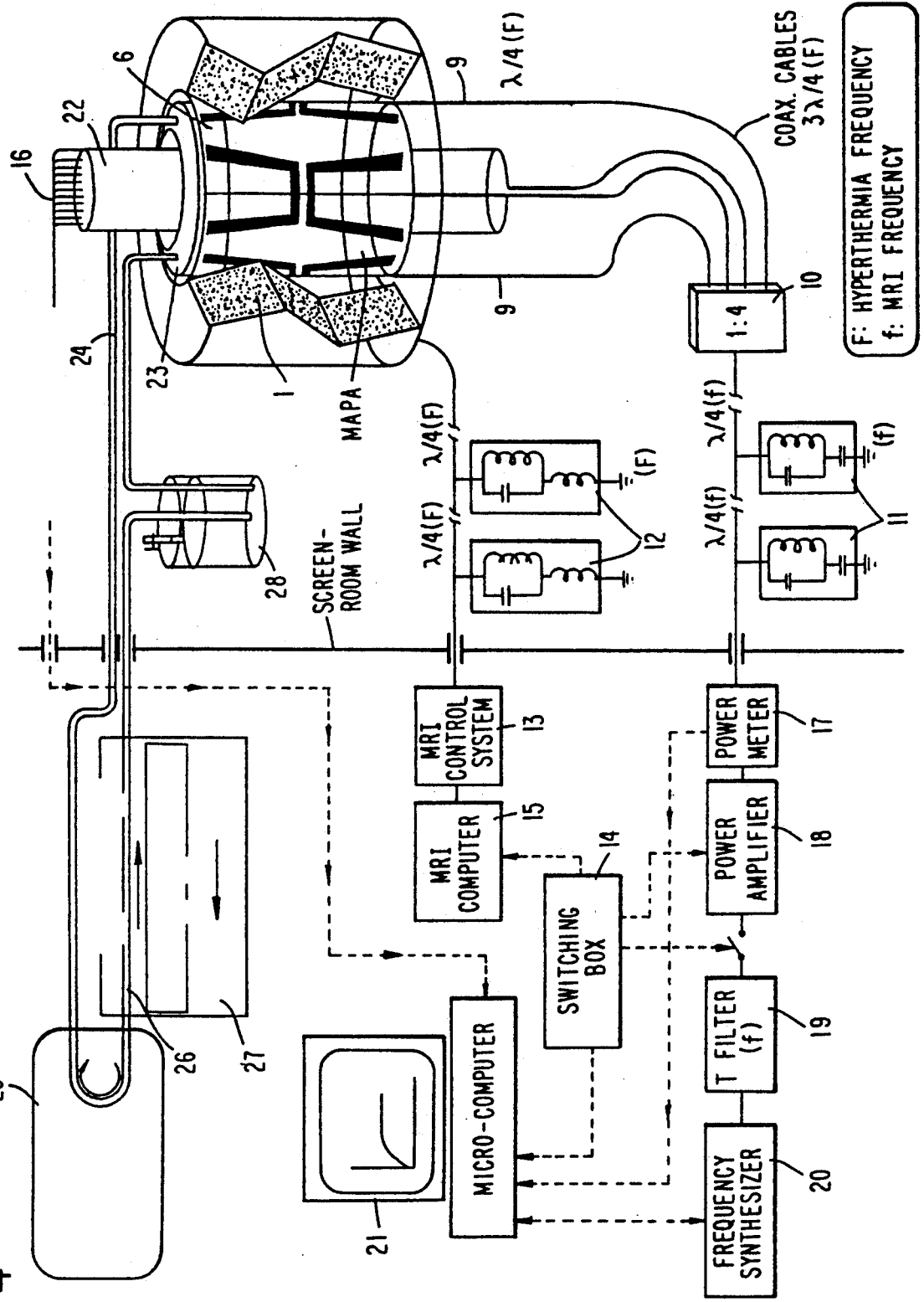
FIG. 4 shows the connections between the MRI probe, the MRI unit, the hyperthermia applicator and the filters.

This embodiment of the invention is described in FIG. 4 in detail.

Also another preferred embodiment of the invention relates to another apparatus which further comprises MRI operably connected to the MRI probe means;

power means operably connected to the hyperthermia applicator and providing a specified output thereto; and a computer operably connected to the MRI and the power means, whereby when the MRI unit detects a variation in the temperature of the subject's body part greater than a predetermined value the computer modifies the output of the power means accordingly to correct the amount of radiant energy transmitted by the applicator to the body part to counter the temperature change.

This embodiment of the invention is also described in some detail in FIG. 4 of this patent. The cooling means and the MRI unit described above are in general known in the art as are the parts utilized therein in the way they function. Accordingly, they are not described herein in further detail.

The MRI signal generated by the body must be purged of any radiofrequency pollution emanating from the hyperthermia applicators. The hyperthermia applicator is thus connected to its power driver via a series of filters tuned at the MRI frequency. The filters prevent the MRI receiver to be damaged by the hyperthermia system and vice-versa. Similarly, the MRI receiver is protected with similar filters tuned at the hyperthermia frequency.

Although this design may be enough to protect the MRI system from damages, a more preferred embodiment has the MRI unit and the hyperthermia system working in a time-sharing process.

A purpose for including a switching means is to alternate periods of heating and MRI recording in a time-sharing manner to avoid any saturation of the MRI preamplifier by the hyperthermia system.

The hyperthermia/MRI probe may thus be utilized by alternation of heating and MRI recording periods in a time-sharing process in a preferred embodiment.

The invention will now be described by means of various embodiments thereof with reference to the figures accompanying this patent.

FIG. 1 shows a diagram of a typical MRI unit. An rf coil (1) is situated inside the magnet (2). This coil (1) is used for both exciting the nuclei and recording the MR signal. Gradient coils (3) are used for image encoding. Pulse sequencing is monitored by the process controller (4) and images are generated using a computer (5).

Figure 2:
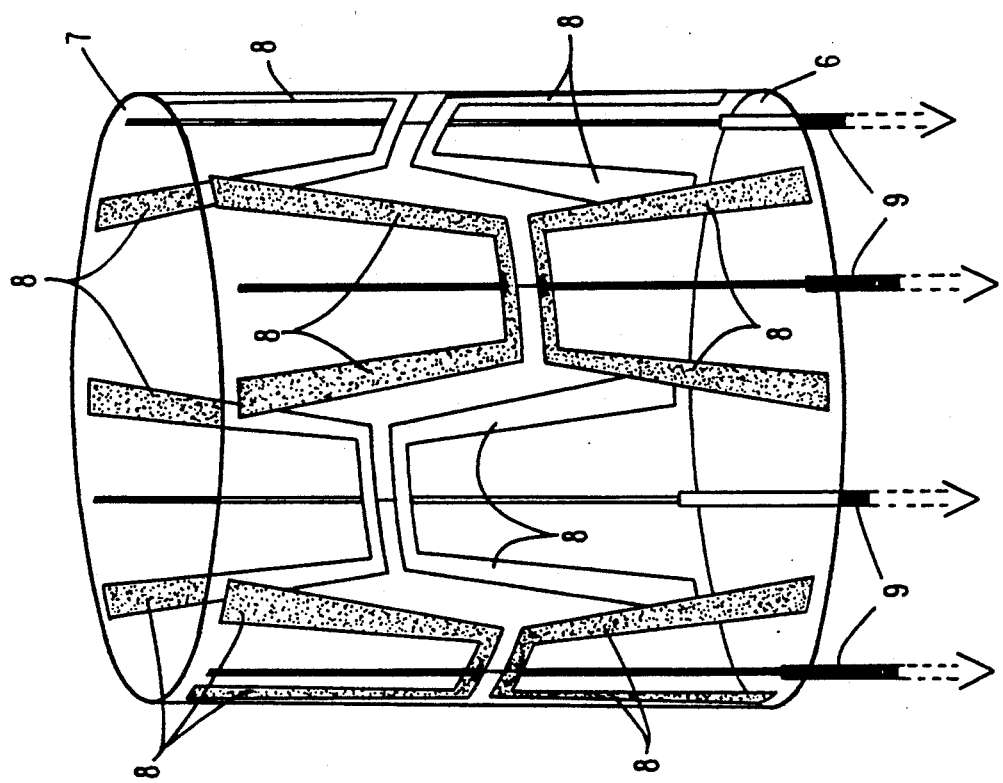
FIG. 2 shows the novel mini-annular phased array (MAPA) radial-frequency hyperthermia applicator which is utilized in the novel hyperthermia applicator/MRI probe of the invention.

FIG. 2 shows the novel improved MAPA hyperthermia applicator (6) designed to be compatible with a whole body MRI unit. The MAPA (6) shown is 25 cm in diameter and 30 cm in length and fits within the MRI head coil (1) is shown in FIG. 4. The frame (7) consists of a thin wall (0.5 cm thick) Plexiglas ® cylinder. Four, axially oriented, trapezoidal double dipoles antennas (8) are evenly spaced on the frame's internal circumference. The antennas (8) are constructed from very thin (30 μm) copper film to minimize eddy currents during gradient switching. All ferromagnetic components which were part of the original MAPA design were eliminated. Typically, the dipoles of the improved MAPA (6) are activated at a single frequency with signals of equal amplitude and phase in order to maximize the energy deposition at the center of the applicator. To maximize the coupling between the improved MAPA (6) and the subject's body part being heated and to enable surface cooling, a fluid-filled bolus (23) as shown in FIG. 4 is used to fill the space between the dipole arrays (8) and the subject's body.

Figure 3:
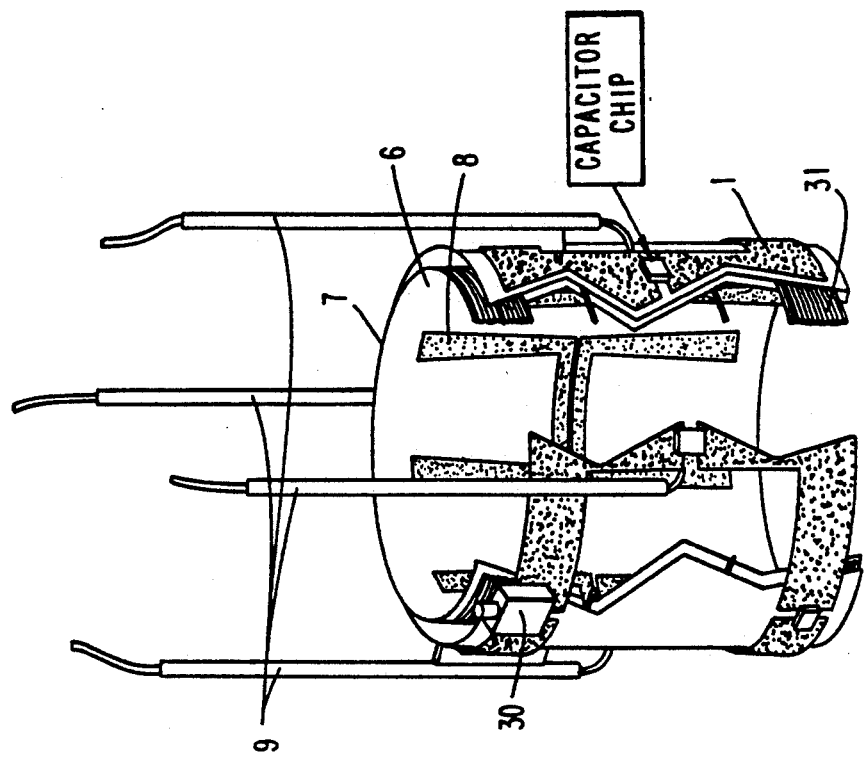
FIG. 3 shows a general diagram of the hyperthermia applicator/MRI probe system of the invention.

FIG. 3 shows a general diagram of the hyperthermia applicator/MRI probe (1; 6). The hyperthermia applicator (MAPA) (6) consists of dipole antennas (8) evenly spaced on a frame (7). The frame is located inside the MRI probe (1) which has a tuning/matching circuit (30) The hyperthermia applicator is fed by baluns (9). Between the hyperthermia applicator (6) and the MRI probe (1) is a Z-gradient coil (31) for use in diffusion imaging and/or fast acquisition of images.

FIG. 4 shows a general functioning diagram of an embodiment of combined HT-MRI apparatus of this invention with its connection to the MRI unit. The right hand side of the drawing illustrates the components which reside inside the MRI screen room. The MAPA (6) is situated inside the head coil (1) of the MRI unit. It is activated with radiofrequency (rf) power via baluns (9), a power divider (10), and a pi filter (11). Another pi filter (12) is also used on the MRI coil (1) to protect the MRI receiver (13), and a switching box (14) serves as the master clock for the heating/imaging time sharing process. Invasive temperature measurements are recorded within the phantom using either thermocouples whose readings are manually logged or fiberoptic probes whose readings are automatically logged by a microcomputer system. Also shown in FIG. 4 are an MRI computer (15) connected to the MRI control system (13) and the switching box (14), thermometer(s) (16) for measuring temperature at the target site, a power meter (17), power amplifier (18), a T filter (19), a frequency synthesizer (20) and a microcomputer (21). The microcomputer (21) receives information on temperature variations from the thermometer(s) (16) and feeds information to the HT applicator (6) to regulate its output. FIG. 4 also shows a temperature control system to maintain the temperature in the area surrounding the treated area. It consists of cooling means (24), a pump (25), a heat-exchanger (26), a thermostatic pumping system (27) and a bubble trap (28).

Figure 5:
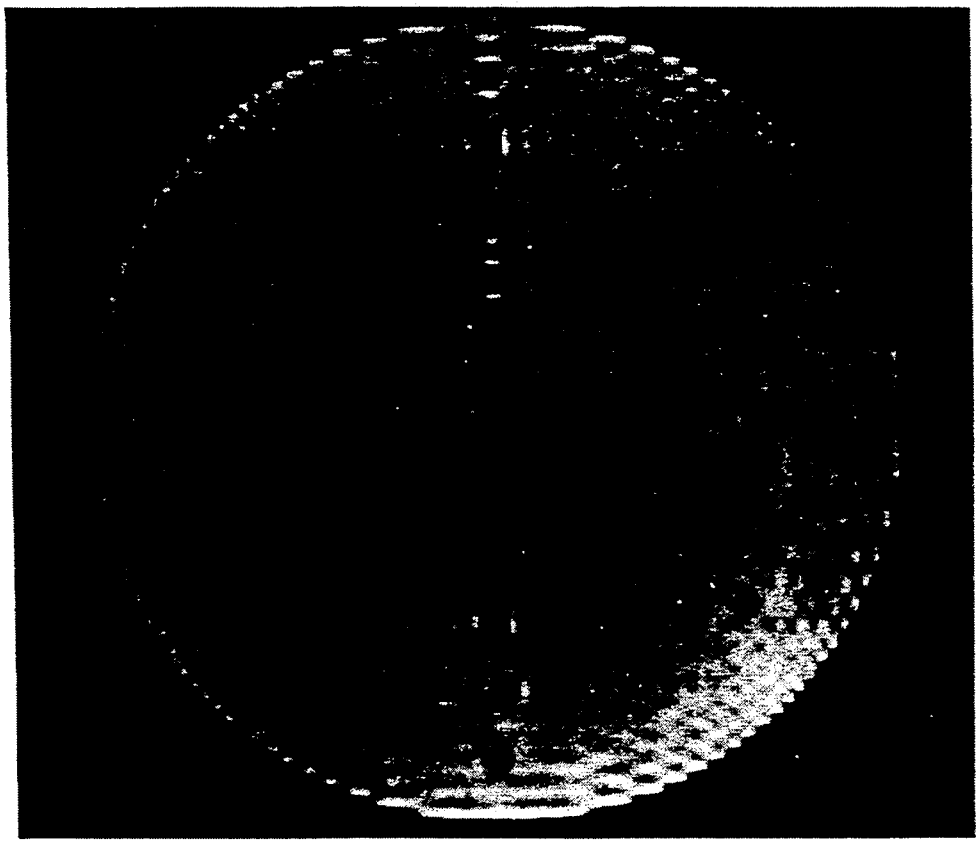
FIG. 5 shows an MR gradient-echo image of a phantom obtained with the MAPA and all supporting baluns, power divider and filters utilized in the examples.

FIG. 5 shows an MR gradient-echo image of a phantom with the combined HT applicator (MAPA)/MRI probe (1; 6) and all supporting baluns (9), power divider, and filters (11;12) in place. The bolus (23), which consists of a PVC bag of a paramagnetic solution of manganese chloride (1 mM/l) and water, is almost invisible and produces substantially no artifacts. The polyacrylamide phantom (22) is clearer because it contains copper sulfate. The temperature measurement catheter(s) (16) are also visible. The MAPA (6) itself is invisible because it contains no water. Neither artifacts nor distortions are produced which may be due to the presence of the MAPA (6).

Figure 6:
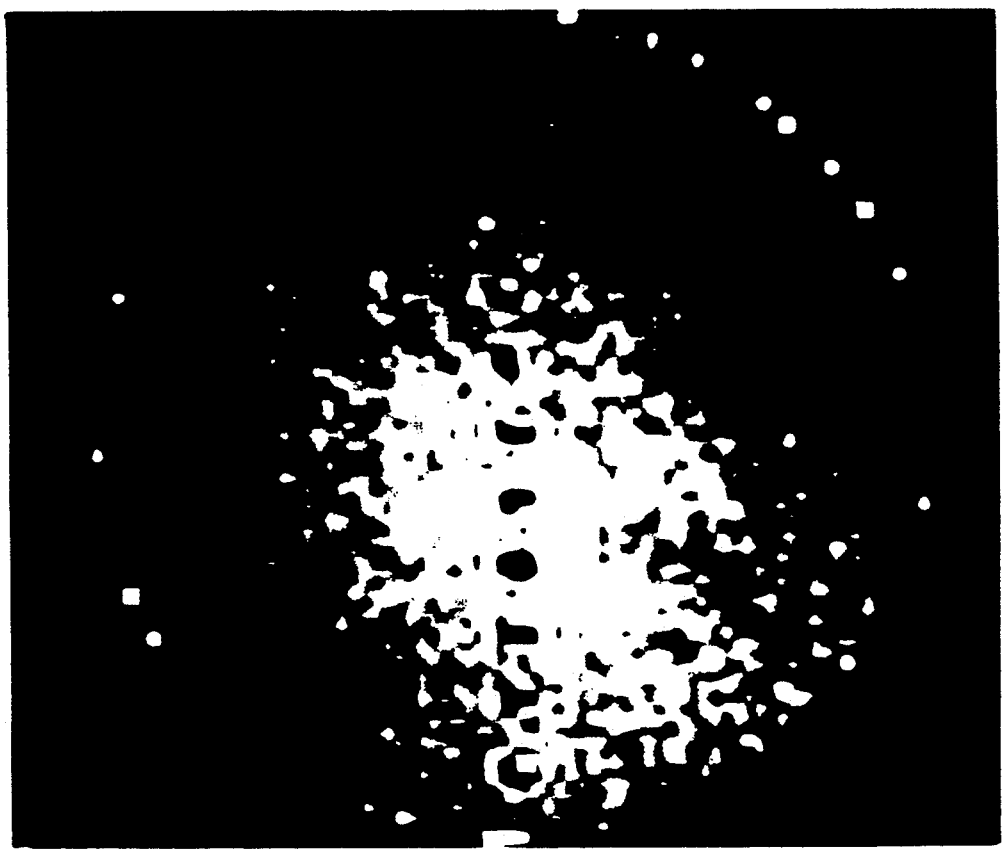
FIG. 6 shows a temperature image obtained during hyperthermia using a homogenous phantom.

FIG. 6 shows a temperature image obtained during hyperthermia using a homogeneous phantom (22). This temperature image was computed using the MRI unit's computer system (5) from diffusion images recorded before and during heating in accordance with another embodiment of the invention. The acquisition time is 7 minutes. The temperature can be read directly on the MRI console by moving its cursor to any location within the picture or to plot a thermal profile computed from a selected region of interest (ROI). High intensity points located in the vicinity of the thermometers (16) and the phantom's (22) shell are calculation artifacts on no signal zones.

Figure 7:
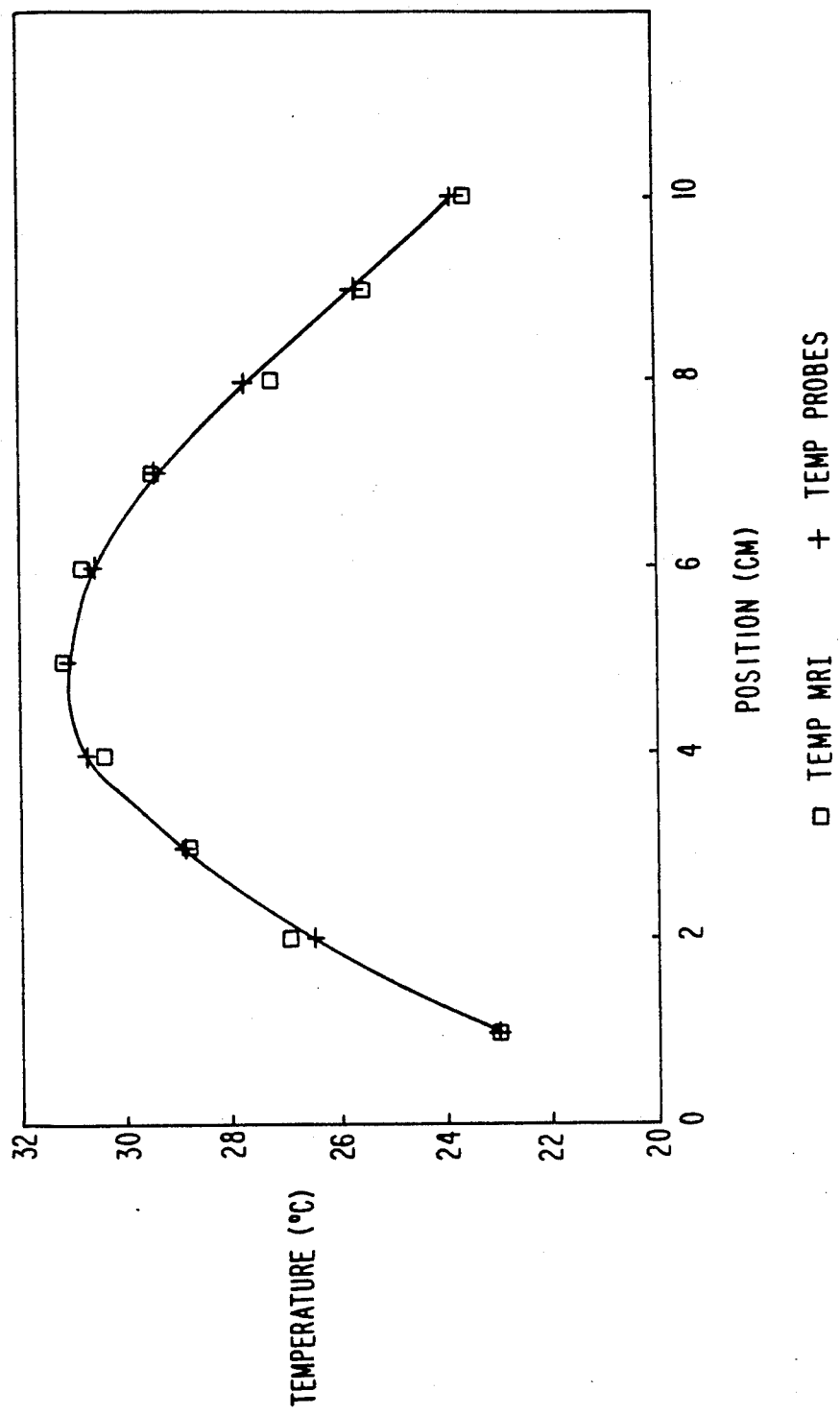
FIG. 7 shows a correlation between MRI (non-invasive) and standard probe (invasive) temperature measurements.

FIG. 7 shows a correlation between MRI (non-invasive) temperature measurements in accordance with this invention and standard probe (invasive) temperature measurements. Standard thermal probes were used to record a profile within the catheter plane plus symbols unfilled boxes show the average of temperatures measured in two regions of interests utilizing MRI measurements, one on each side of the catheter plane. The resolution is better than 1° C. with a 5 mm spatial resolution.

Figure 8:
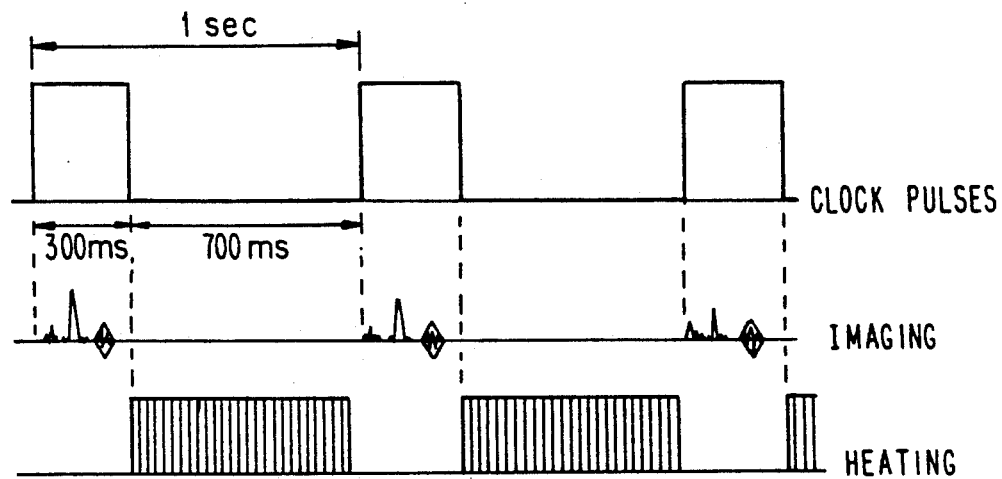
FIG. 8 shows a diagram of the time sharing process used to alternate heating periods with MRI recording periods.

FIG. 8 shows a diagram of the time sharing process used to alternate heating periods with MRI recordings. As discussed above, the switching box (14) serves as a master clock for heating/imaging time sharing process as illustrated in FIG. 8.

Figure 9:
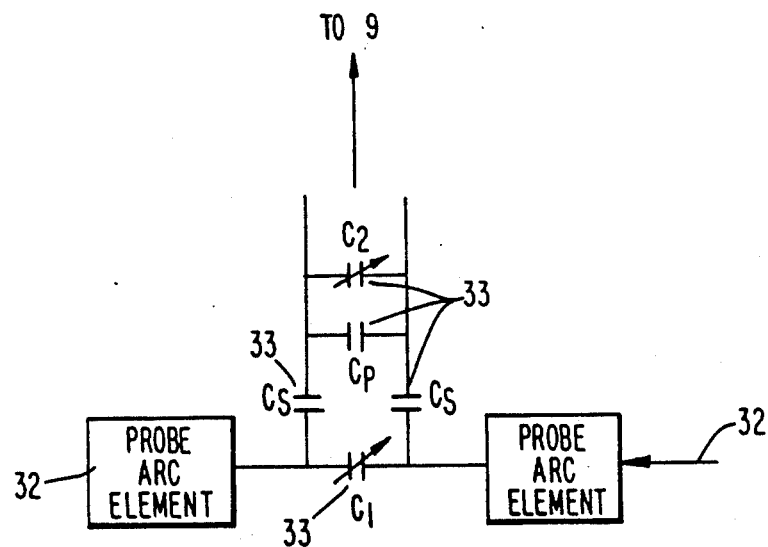
FIG. 9 shows an electrical diagram of the MRI probe.

FIG. 9 shows an electric diagram of an MRI probe (split Alderman-Grant). The baluns (9) are connected to the tuning/matching pad to form balanced feeding. The tuning and matching circuit (30) is made of capacitors C1, C2, Cp and Cs (33). The tuning/matching pad (33) is connected to the probe arc elements (32).

In a particularly preferred embodiment the mini-annular phased array (MAPA) is that described by Guerquin Kern et al, Medical Physics 14:674 (1987).

In another particularly preferred embodiment of the invention the Z magnetic gradient coil is that described in Mansfield and Turner, GB application No. 8,714,434 filed on Jun. 19, 1987.

To use MRI to monitor temperature and to measure perfusion during hyperthermia it is necessary to combine a hyperthermia device with an MRI unit. This combination is not a priori trivial since each device will be functionally disturbed, and possibly damaged, by the presence of the other. This technical challenge has been overcome by the present inventors in a manner which is described herebelow.

Having now generally described this invention, the same will be better understood by reference to certain specific examples, which are included herein for purposes of illustration only and are not intended to be limiting of the invention or any embodiment thereof, unless so specified.

EXAMPLES

Example 1: Whole Body MRI System

We used a whole body MRI system (Magniscan 5000, Thomson-CGR) working at 21 MHz with an about 0.5 tesla magnetic field in combination with a mini-annular phased array (MAPA) radio-frequency HT applicator which had previously been designed to treat limb tumors (Turner, P. F. IEEE Trans, MTT 34: 508–513 (1986); (Guerquin-Kern, J-L, et al, Medical Physics 14: 674–680 (1987); (Charny, C. et al, Medical Physics 13: 449–456 (1986); (Charny, C. et al, Medical Physics 15: 17–23 (1988)).

Example 2: MAPA for use with MRI System for use in Accordance with Preferred Embodiment of the Invention The MAPA's outer diameter, originally about 30 cm, was reduced to 25 cm to fit within the MRI system's head coil, while its length was kept at about 30 cm (see, FIG. 2). The MAPA's frame is a thin wall, about 0.5 cm thick, Plexiglas ® cylinder. Four, axially oriented, double, trapezoidally-shaped dipole antennas are evenly spaced on the frame's internal circumference. The antennas are constructed from very thin (about 30 μm) copper film in order to minimize eddy currents during gradient switching. All ferromagnetic components contained in the original design were eliminated.

Typically, the dipoles of the MAPA are activated at a single frequency with signals of equal amplitude and phase in order to maximize the energy deposition at the center of the applicator (Turner, P. F. IEEE Trans, MTT 34: 508–513 (1986); (Guerquin-Kern, J-L, et al, Medical Physics 14: 674–680 (1987); (Charny, C. et al, Medical Physics 13: 449–456 (1986)).

It is possible, however, to vary the MAPA's power description pattern by activating each dipole using rf signals differing in frequency, phase and/or amplitude (Charny, C. et al, Medical Physics 15: 17–23 (1988)). The MAPA can also operate anywhere in the frequency range of approximately 100 to 200 MHz. A single working frequency of 168 MHz (i.e. 8 times the MR frequency) was chosen to simplify construction of the appropriate baluns and filters.

To maximize the coupling between the MAPA and the extremity being heated (i.e., to achieve a good "match") and to enable surface cooling, a fluid-filled deformable plastic bolus is used to fill the space between the dipole arrays and the limb.

Each antenna is supplied with rf power via an about 50 Ω non-ferromagnetic coaxial cable (RG-58) balanced with a 168 MHz, lambda/4, bazooka-type balun which is linked to a 1:4 power divider via a ⅜ (at 168 MHz) line (see, FIG. 3).

The baluns are axially oriented. In order to prevent any capacitive interaction with the dipole antennas the baluns are not physically attached to the MAPA at the center of each dipole array. Rather, they are connected to the centers by about 15 cm lengths of RG-58 coaxial cable, additional 15 cm pieces being attached on the other sides of the dipoles to ensure symmetry (see, FIG. 2).

Example 3: Setting up an Applicator Probe in Accordance with a Preferred Embodiment of the Invention The power divider was connected by a high power, low-loss 50 Ω coaxial cable (Belden 9913, RG-8 type), via a grounded bulkhead fitting through the screen room wall to a 1 kW cw broadband amplifier (Instruments for Industry Model 406) located outside the screen room. This 50 Ω power line included a $\pi$ section filter, located between the MAPA and the screen room wall. The filter consisted of a 4 (at 21 MHz) line at each end of which were two identical resonant circuits to "ground".

Each circuit consisted of a parallel resonating circuit adjusted for 168 MHz combined with a series circuit resonating at 21 MHz. The rest of the line between the MAPA and the HT amplifier had no particular prescribed length. The $\pi$ filter thus rejected 21 MHz with no significant attenuation at 168 MHz, thereby effectively preventing the MRI rf pulses from damaging the HT electronic equipment and ensuring that no interference reached the MRI receiver.

The HT amplifier was driven by a solid-state signal generator (Fluke Model 6060A). Forward and reflected power were monitored by a 438A Hewlett-Packard bi-directional power-meter with two 8482A power sensors using a high power, dual directional coupler (Amplifier Research Model DC 2000).

All equipment for the HT system was positioned outside the screen room as far from the magnet as possible in order to minimize any effects from the fringe magnetic field of the MR unit.

The large electric fields generated by the MAPA can capacitively couple to the MRI system's head coil. Thus the MRI receiver had to be protected with a $\pi$ filter, similar to that described above, that rejected 168 MHz while giving negligible attenuation at 21 MHz. Although this protected the MRI pre-amplifier against damage, it could still be saturated during heating, making imaging impossible. Since further filtering degraded the MR unit's signal-to-noise ratio, it was therefore necessary for us to heat the image in a time sharing manner. A blanking circuit on the HT rf power amplifier was used to deactivate the power supply of the last stage of the IFI unit and thereby block any rf noise issuing therefrom. In addition, a pin-diode switch between the signal generator and the amplifier was used. A T filter ($-40$ dB) was also inserted between the rf generator and the amplifier to stop passively any 21 MHz signal (emitted inadvertently from the signal generator) from damaging the MR unit's preamplifier.

Example 4: Interphasing in a Preferred Embodiment of the Invention

To control the heating/imaging time-sharing process, a switch box was constructed. For the MRI system, this switching unit was connected to the "cardiac gating" input normally used to synchronize imaging with electrocardiographic (ECG) signals. For the HT system, the switching unit was connected to both the pin diode switch located between the signal generator and the amplifier and to the blanking circuit of the amplifier. To avoid "blanking" the rf amplifier in the presence of an rf input signal, the amplifier was switched on 5 ms before, and off 5 ms after, the pin diodes. Imaging was performed between the heating periods. The total heating-/imaging cycle was set to a 1 second repetition time (TR), which corresponded to a 700 ms heating period during the "dead time" of each MRI acquisition cycle. In this way imaging and heating could be achieved efficiently with no time wasted.

Example 5: Additional Computerized Control Feature in Preferred Embodiment of the Invention The HT system was controlled by a PC/AT clone computer which was digitally connected to (1) the rf signal generator and rf power meter via IEEE-488 interface and (2) the rf amplifier via 4 input and 4 output digital lines. The keyboard and monitor of the PC/AT were extended to the MRI console room by a serial communication link so that both the HT and MRI systems could be monitored conveniently.

Example 6: Elimination of Vibrations

A special plastic support was made to fasten the MAPA rigidly to the MRI's mobile patient support table and the table's guide trace (See, FIG. 4). To minimize motion artifacts due to the mechanical vibrations induced by the gradient coils, the MAPA was not permitted to make contact with any other part of the MRI unit.

Example 7: Supply of Fluid to the MAPA/MRI Combination

The MAPA's bolus fluid was supplied via a closed circuit pumping system which included the following.
(1) a pulse-free, rf noise-free (a synchronous motor), centrifugal pump,
(2) a tube-in-shell heat exchanger,
(3) a bubble trap, and
(4) 1.5875 cm ($\frac{5}{8}$") i.d. reinforced PVC tubing.

A thermostatically regulated pumping system situated outside the screen-room was used to adjust the bolus coolant temperature via the heat exchanger located within the screen room. Water flow through the screen room wall was achieved by passing the PVC water lines through two wave guides (20 cm in length, 3 cm in diameter) located in the screen room wall.

Example 8: Avoiding Interference from Movement of Subject

Since MRI is very sensitive to overall movements of the object to be imaged, a paramagnetic solution of manganese chloride (1 mM/l) was used instead of distilled water as the bolus fluid.

The manganese chloride did not affect the dielectric properties of the bolus fluid sufficiently to modify the MAPA's power deposition pattern, but it did decrease dramatically the bolus fluid's relaxation time so that, with the appropriate imaging sequence, the signal coming from the bolus was negligible compared to that coming from the phantom. Because the bolus fluid was not visible in the diffusion and derived-temperature images, it could be circulated during imaging.

Example 9: Testing the Apparatus in Accordance with Preferred Embodiment of the Invention The complete HT-MRI system was tested using a leg phantom. This phantom consisted of a 12 cm internal diameter, 60 cm long thin-wall (0.5 cm) Plexiglas® tube filled with polyacrylamide gel (92.5% water) doped with copper sulfate (5 mM/l) so that the relaxation times were close to those expected in vivo. Eleven 16 ga. Teflon® catheters (2 mm outer diameter) were also placed longitudinally, 1 cm apart, within the gel, permitting us to insert thermal probes.

Example 10: Invasive Temperature Measurements Made in Accordance with the Prior Art Invasive temperature measurements were made using either fiber optic probes or thermocouples. The fiber optic system consisted of a Luxtron Model 3000 fluoroptic 8 channel system, which was located inside the screen room, and 8 Luxtron MPM 0.7 mm o.d. single point thermal probes. By means of a fiber optic RS 232 link though the screen room wall, data from the Luxtron unit were logged in real-time by the PC/AT computer system located outside the screen room. The thermocouple system consisted of a digital thermometer (Bailey Sensortek Model BAT-12) and 11 miniature (0.23 mm o.d.) Teflon ® coated probes having a very short time constant (0.1 s). Because these thermocouples are sensitive to rf fields, thermocouple temperatures were recorded manually during short periods when both the HT and MR were quiescent.

Example 11: Non-invasive Temperature Measurements Made in Accordance with This Invention To test our ability to image through the MAPA, an initial series of tests was performed in the absence of any HT rf power using sequences that were sensitized to rf and magnetic field inhomogeneities (e.g. gradient echo).

Later on, hyperthermia sessions were performed on phantoms using a 1 Hz, 70% duty cycle (e.g., HT heating for 700 ms and MR imaging for 300 ms every second). During these simulated hyperthermia sessions, the MAPA cooling system was adjusted to obtain a temperature of about 15° C. with the bolus.

The phantom was initially heated with 300 W of rf power for 30 minutes. This produced a temperature gradient of about 13° C. within the phantom (e.g. $\approx 33°$ C. at the center of the phantom and about 20° C. at the most peripheral catheter).

The HT rf power was then reduced to about 100 W to maintain a steady state. After an additional about 15 min, a diffusion image was recorded over a time period of 7 minutes. A temperature image was then computed immediately using the MRI's processing system which consists of a DEC VAX-11/730 computer coupled to an MSP-3000 array processor.

Example 12: Compatibility of MAPA and MRI Systems

Images were first recorded using pulse sequences sensitized to rf and magnetic field inhomogeneities (e.g., gradient-echo). No artifacts or other distortions were found (see, FIG. 5). We therefore concluded that the physical presence of the MAPA did not interfere with the normal functioning of the MRI system.

Before beginning the heating studies, several additional compatibility tests were performed. First, the "cross-talk" between the two systems was found to be less than 600 mV at the MRI receiver input when the MAPA was being activated with 1 kW cw. Second, the presence of both the miniature thermocouples and the fiber-optic probes was not detectable in any of the images. Also, these particular sensors and their electronic control units produced no artifacts.

Example 13: Temperature Imaging During Hyperthermia

A temperature image computed in real-time from steady-state diffusion images recorded before and during a heating is shown in FIG. 6. The pixel size is 2 mm×2 mm (128×128 pixels) and the slice thickness is 20 mm. Brightness is directly proportional to temperature. Consequently, it is possible to read directly the temperature on the MRI console by moving the cursor to any location within the picture or to plot a thermal profile computed from a selected region of interest (ROI).

Because the phantom was not centered exactly with the MAPA, it can be seen that the point of maximum energy deposition (i.e., the "hot spot") was not exactly at the center of the phantom but shifted slightly downwards. It can also be noted that the manganese chloride solution used for the circulating coolant makes the bolus virtually transparent.

To avoid catheter zones where no MR signal was recorded, temperature profiles were recorded from ROIs 1 cm wide and 11 cm long on both sides of the catheter plane. The mean of these measurements, recorded symmetrically every 5 mm along the two ROI profiles, together with the temperatures recorded by the probes within the catheters, which were spaced 1 cm apart, can be seen in FIG. 7. The correlations between our non-invasive and invasive temperature measurements are good and confirm our previously reported preliminary results (Simpson, J. H. and Carr, H. Y., Phys. Rev. 111: 1201-1202 (1958)) LeBihan, D. et al, Radiology 171: 853-587 (1989)).

Example 14: Discussion of Results and Other Applications of the Invention

These studies have shown that an HT and a MR system can be combined to monitor temperature non-invasively during clinical hyperthermia. Furthermore, because high resolution standard MR anatomical images are readily available and can be superimposed on the temperature images the apparatus of the invention greatly facilitates the localization of the heating pattern within the tumors so that normal tissues can be spared the deleterious effects associated with high temperatures. In addition to monitoring temperature during hyperthermia, MRI can be used for monitoring perfusion (Simpson, J. H. and Carr, H. Y., Phys. Rev. 111: 1201-1202 (1958))LeBihan, D. et al, Radiology 171: 853-587 (1989); LeBihan, D. et al, Radiology 168: 497-505 (1988)) and various metabolic processes during heating (Vaupel, P. W. et al, Proc. SMRM, Vol. 1, p. 412 (1988)).

From the results using muscle equivalent phantoms a measured temperature resolution of about 0.5° C. and spatial resolution of about 5 to 10 mm appears adequate for clinical purposes. The current time scale of 7 mn for the acquisition of a temperature image, however, limits the monitoring to steady-state situations.

This limitation can be overcome by implementing fast imaging techniques such as steady-state free precession (LeBihan, D. Magn Reson Med. 7: 346-351 (1988)) and echo-planar imaging (Turner, R. and LeBihan, D. J. Mag. Res. (1989). In press). These two imaging methods have recently yielded diffusion images and therefore will permit real-time non-invasive temperature monitoring.

Other types of electromagnetic or ultrasonic hyperthermia applicators can be used with MRI as well. All will face similar compatibility problems.

Example 15: Description of Split Alderman-Grant 64 MHz Probe

This is a probe used in a GE Signa 1.5T imager in conjunction with fast switching gradients and a 168 MHz hyperthermia probe. The design of the probe is a modified Alterman and Grant type probe (Alderman, D. G. and Grant, D. M., J. Magn. Reson. 36, 447 (1979); Hoult D. I., Chen C-N and Sank, V. J., Magn. Reson. Med. 3, 730 (1986)) with balanced feeding scheme.

The probe's physical dimensions are as follows.

Diameter: 30.5 cm.
Length: 27.5 cm.
Width of vertical elements: 22.0 cm. (corresponds to 80 degrees).
Length of vertical elements: 17.7 cm, in the middle.
Width of ring elements: 6.4 cm.
Partial guard strips: 10 cm long, 6.5 cm wide 0.65 cm away from the inside of the probe, and directly opposite to the capacitors of the ring elements.
Shield: 2.3 cm away from the outside of the probe.
16 elements with each 2.76 cm wide, 30.5 cm long symmetrically distributed around the probe.

Electrical description:
Capacitors connecting the ring elements: 33 pf (shown as the capacitor c below).
Capacitors connecting the vertical elements: 33 pf (shown as b in gray).
Matching and tuning pad (constitutes c in graph):
Cs: 68 pf
Cp: 68 pf
C1 and C2 are variable capacitors matching to 50 Ohms.

The balun connected to the pad to form balanced feeding is shown in FIG. 9.

When loaded with a water bolus, which is doped with 5 mM $MnCl_2$, between the hyperthermia probe and a phantom (12.5 cm in diameter, length extends well beyond the probe length, filled with gelatin which has been mixed with 5 mM $CuSO_4$), the Q is about 30 inside the magnet.

The invention now being fully described, it will be apparent to one of ordinary skill in the art that many changes and modifications can be made thereto without departing from the spirit or scope of the invention as set forth herein.

We claim:

1. An apparatus for hyperthermia treatment of a subject wherein the temperature of the subject's body part being treated may be controlled within about ±0.5° C., comprising:
   an MRI probe which includes a tuning/matching circuit and a radiofrequency coil for receiving and transmitting magnetic resonance signals, said tuning/matching circuit and radiofrequency coil being connected to one another, the radiofrequency coil receiving a rotating field signal induced by the subject's body part;
   a hyperthermia applicator for transmitting radiant energy, said hyperthermia applicator being positioned inside the MRI probe and being provided with an inner surface for exposure to a subject's target body part to be treated;
   said MRI probe being positioned inside a magnet and capable of providing information for detecting a variation in the temperature of the subject's body part being treated;
   a magnetic gradient coil encoding diffusion images, said magnetic gradient coil being positioned outside the hyperthermia applicator; and
   a filter connected to at least one of the hyperthermia applicator and the MRI probe to isolate signals thereof from one another, wherein all components of the probe, the applicator and the gradient coil are made of substantially non-ferromagnetic materials.

2. The apparatus of claim 1, further including an MRI control unit, the MRI control unit being connected with the MRI probe for receiving the information provided by the MRI probe and detecting from said information a variation in the temperature of the subject's body part.

3. The apparatus of claim 2, further including
   power means connected to the hyperthermia applicator for providing a specified output thereto;
   computer means connected to the MRI control unit and the power means, whereby when a variation in the temperature of the subject's body part greater than a predetermined value is detected by the MRI unit, the computer means modifies the output of the power means to correct the amount of radiant energy transmitted by the hyperthermia applicator to the body part to counter the temperature change.

4. The apparatus of claim 3, further including a conformable plastic filler covering the surface of the hyperthermia applicator and being capable of transmitting radiant energy from the hyperthermia applicator to the subject's body part to be treated.

5. The apparatus of claim 4, wherein the conformable filler contains water doped with a compound which renders the filler invisible in MRI images.

6. The apparatus of claim 4, further comprising:
   cooling means for cooling the conformable filler;
   a pump connected to the cooling means;
   a heat-exchanger connected to the heat-exchanger for measuring the temperature of the conformable filler and for activating the heat-exchanger means and the cooling means to maintain the temperature of the conformable filler with a desired range.

7. The apparatus of claim 3, wherein the hyperthermia applicator comprises a mini annular phased array (MAPA) comprising antenna means for receiving power from the power means and transmitting radiant energy to the subject's body part to be treated.

8. The apparatus of claim 7, wherein the antenna means comprises:
   four pairs of dipole antennas, the members of each pair of dipole antennas being symmetrically positioned about the hyperthermia applicator inner surface.

9. The apparatus of claim 8, wherein the dipole antennas comprise a copper film of about 5 to 100 $\mu m$ thick.

10. The apparatus of claim 1, wherein the magnetic gradient coil is selected from the group consisting of X-axis, Y-axis and Z-axis gradient coils and combinations thereof.

11. The apparatus of claim 1, wherein the hyperthermia applicator comprises means for transmitting radiofrequency waves.

12. The apparatus of claim 11, wherein the hyperthermia applicator comprises radiofrequency capacitive applicators.

13. The apparatus of claim 11, wherein the hyperthermia applicator comprises a radiation applicator.

14. The apparatus of claim 1, wherein the hyperthermia applicator comprises means for transmitting microwaves.

15. The apparatus of claim 14, wherein the hyperthermia applicator comprises wave guides.

16. The apparatus of claim 14, wherein the hyperthermia applicator comprises microstrip applicators transmitting microwave radiation of about 300 MHz to 5GHz.

17. The apparatus of claim 1, wherein the hyperthermia applicator comprises means for transmitting ultrasound waves.

18. The apparatus of claim 17, wherein the hyperthermia applicator comprises piezo-electric applicators.

19. An apparatus for hyperthermia treatment of a subject wherein the temperature of the subject'body part being treated may be controlled within about ±0.5° C., comprising:

an MRI probe which includes a tuning/matching circuit and a radiofrequency coil for receiving and transmitting magnetic resonance signals, said tuning/matching circuit and radiofrequency coil being connected to one another, the radiofrequency coil receiving a rotating field signal induced by the subject's body part;

a hyperthermia applicator for transmitting radiant energy, said hyperthermia applicator being positioned inside the MRI probe and being provided with an inner surface for exposure to a subject's target body part to be treated;

said MRI probe being positioned inside a magnet and capable of providing information for detecting a variation in the temperature of the subject's body part being treated;

an MRI unit connected to the MRI probe for receiving the information provided by the MRI probe and the detecting from said information a variation in the temperature of the subject's body part;

power means connected to the hyperthermia applicator for providing a specified output thereto;

computer means connected to the MRI unit and the power means, whereby when a variation in the temperature of the subject's body part greater than a predetermined value is detected by the MRI unit, the computer means modifies the output of the power means to correct the amount of radiant energy transmitted by the hyperthermia applicator to the body part to counter the temperature change;

filter means connected to at least one of the hyperthermia applicator and the MRI probe to isolate signals thereof from one another; and a conformable filler covering the surface of the hyperthermia applicator and being capable of transmitting radiant energy from the hyperthermia applicator to the subject's body part to be treated, said conformable filler containing water doped with a paramagnetic compound so that the filler is not visible in MRI images and does not produce artifacts in such images;

wherein all components of the probe, the applicator and the conformable filler.

* * * * *